United States Patent [19]

Stähle et al.

[11] 4,166,859
[45] Sep. 4, 1979

[54] 2-BROMO-6-FLUORO-N-(2-IMIDAZOLIDINYLIDENE)-BENZAMINE AND SALTS THEREOF AND THE USE TO TREAT HYPERTENSION

[75] Inventors: Helmut Stähle; Herbert Köppe; Werner Kummer, all of Ingelheim am Rhein; Wolfgang Hoefke, Budenheim, all of Fed. Rep. of Germany

[73] Assignee: Boehringer Ingelheim GmbH, Ingelheim am Rhein, Fed. Rep. of Germany

[21] Appl. No.: 808,409

[22] Filed: Jun. 20, 1977

[30] Foreign Application Priority Data

Jul. 3, 1976 [DE] Fed. Rep. of Germany ....... 2630060

[51] Int. Cl.² .......................................... A61K 31/415
[52] U.S. Cl. .................................. 424/273 R; 548/337
[58] Field of Search ........................ 424/273; 548/337

[56] References Cited
PUBLICATIONS

Reprint from A.C.S. Symposium Series, No. 27, "Centrally Acting Antihypertensive Agents", pp. 27–53, (1976).
J. Med. Chem. 19(8), pp. 1049–1054, (1976).

Primary Examiner—Stanley J. Friedman
Attorney, Agent, or Firm—Hammond & Littell

[57] ABSTRACT

The compound of the formula

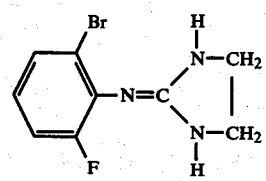

and non-toxic, pharmacologically acceptable acid addition salts thereof; the compound as well as the salts are useful as antihypertensives.

3 Claims, No Drawings

2-BROMO-6-FLUORO-N-(2-IMIDAZOLIDINYLIDENE)-BENZAMINE AND SALTS THEREOF AND THE USE TO TREAT HYPERTENSION

This invention relates to a novel 2-phenylimino-imidazolidine and non-toxic acid addition salts thereof, as well as to a method of preparing these compounds.

More particularly, the present invention relates to a novel compound

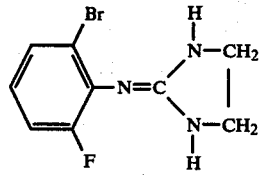

and non-toxic, pharmacologically acceptable acid addition salts thereof.

THE PRIOR ART

2-Phenylimino-imidazolidines have for a long time been of great interest because of their outstanding pharmacologic and therapeutic properties. Therefore, many compounds of this type are disclosed in the prior art, such as in Belgian Pat. Nos. 623,305; 653,933; 687,656; 687,657; and 705,944; as well as elsewhere. The prior art also discloses a variety of processes for the preparation of 2-phenylimino-imidazolidenes.

THE INVENTION

We have discovered that a particular specie of the genus of 2-phenylimino-imidazolidines, namely 2-bromo-6-fluoro-N-(2-imidazolidinylidene)-benzamine and its non-toxic, pharmacologically acceptable acid addition salts, which are not specifically disclosed anywhere in the prior art, have especially desirable and unique pharmacological properties.

The compound of the formula I may be prepared by reacting an isothiourea of the formula

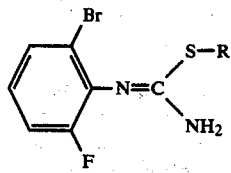

wherein R is hydrogen or alkyl of up to 4 carbon atoms, or an acid addition salt thereof, with ethylenediamine or a salt thereof.

The reaction is preferably carried out at a temperature between 100° and 250° C. in the presence of a polar protic, polar aprotic or non-polar solvent medium; it may, however, also be performed in the absence of a solvent at elevated temperatures. The reaction period varies between a few minutes and several hours.

The starting compounds of the formula II may be obtained by reacting 2-bromo-6-fluoro-aniline with potassium thiocyanate and benzoyl chloride, followed by hydrolysis with potassium hydroxide to form the corresponding thiourea of the formula II which may be converted into an isothiouronium salt of the formula II by alkylation with an alkylating agent, such as an alkyl halide or a dialkyl sulfate. An S-alkyl-isothiourea of the formula II may be obtained by acid cleavage of the isothiouronium salt with potassium hydroxide.

The compound of the formula II is an organic base and therefore forms addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicylic acid, ascorbic acid, methanesulfonic acid, ethanephosphonic acid, 8-chlorotheophylline or the like.

The following example illustrates the present invention and will enable others skilled in the art to understand it more completely. It should be understood, however, that the invention is not limited solely to the particular example given below.

EXAMPLE 1

2-Bromo-6-fluoro-N-(2-imidazolidinylidene)-benzamine and its monohydrochloride

A mixture consisting of 6.7 gm (0.017 mol) of N-(2-bromo-6-fluoro-phenyl)-S-methyl-isothiouronium iodide, 1.7 ml of ethylenediamine (150% of theoretical amount) and 20 ml of n-butanol was refluxed for six hours while stirring. Thereafter, the reaction mixture was evaporated to dryness in vacuo, and the residue was dissolved in dilute hydrochloric acid. The resulting solution was extracted twice with ether, the ethereal extracts being discarded. Subsequently, the acidic aqueous phase was fractionally extracted with ether at stepwise increasing pH-values (alkalization with dilute sodium hydroxide). The thin-layer chromatographically pure fractions were combined, dried over magnesium sulfate and filtered through activated charcoal. The filtrate, which contained 2-bromo-6-fluoro-N-(2-imidazolidinylidene)-benzamine, was admixed with ethereal hydrochloric acid until it reacted acid to Congo Red, whereby a precipitate formed which was collected by suction filtration, washed with absolute ether and dried. 2.7 gm (53.6% of theory) of 2-bromo-6-fluoro-N-(2-imidazolidinylidene)-benzamine monohydrochloride, m.p. 259°–262° C., were obtained. The pKa-value of the product was 8.2 Empirical formula: $C_9H_9BrFN_3$. Molecular weight: 294.54.

The following are the empirical formulas, molecular weights and melting points of other acid addition salts which were prepared in analogeous manner:

| | |
|---|---|
| Hydrobromide: (hygroscopic) | $C_9H_9BrFN_3 \cdot HBr$ <br> mol. weight: 339.01 <br> m.p.: 218°–222° C. |
| Nitrate: (slightly hygroscopic) | $C_9H_9BrFN_3 \cdot HNO_3$ <br> mol. weight: 321.11 <br> m.p.: 147°–148° C. |
| Maleate: | $C_9H_9BrFN_3 \cdot HOOC-CH=CH-COOH$ ($C_4H_4O_4$) <br> mol. weight: 374.16 <br> m.p.: 134°–135.5° C. |
| Oxalate: (hygroscopic) | $C_9H_9BrFN_3 \cdot HOOC-COOH$ ($C_2H_2O_4$) <br> mol. weight: 348.13 <br> m.p.: - (hygroscopic oil) |
| 8-Chlorotheophyllinate: | $C_9H_9BrFN_3 \cdot C_7H_7ClN_4O_2$ <br> mol. weight: 472.69 |

-continued

| | m.p.: 206°–208° C. |
|---|---|
| Tosylate: | $C_9H_9BrFN_3 \cdot C_7H_8O_3S \cdot H_2O$ |
| (hygroscopic) | mol. weight: 448.31 |
| | m.p.: 146°–149° C. |
| Benzoate: | $C_9H_9BrFN_3 \cdot C_7H_6O_2$ |
| (slightly hygroscopic) | mol. weight: 380.21 |
| | m.p.: 194°–196° C. |
| Tartrate: | $C_9H_9BrFN_3 \cdot C_4H_6O_6$ |
| (hygroscopic) | mol. weight: 408.18 |
| | m.p.: 109°–111.5° C. |
| Methanesulfonate: | $C_9H_9BrFN_3 \cdot CH_4O_3S$ |
| (hygroscopic) | mol. weight: 354.20 |
| | m.p.: 182°–184° C. |
| Citrate: | $C_9H_9BrFN_3 \cdot C_6H_8O_7$ |
| (hygroscopic) | mol. weight: 450.21 |
| | m.p.: 106°–108° C. |

As indicated above, the compound defined by formula I and its non-toxic acid addition salts have useful pharmacodynamic properties. More particularly, they exhibit antihypertensive activity in warm-blooded animals, such as rabbits and rats, and are therefore useful for the treatment of various forms of hypertonia.

The unique and unobvious aspect of the pharmacological activity of 2-bromo-6-fluoro-N-(2-imidazolidinylidene)-benzamine and its non-toxic acid addition salts is that the ratio between the primary, desirable hypotensive activity and undesirable side-effects, such as inhibition of stomach juice secretion—as a measure of dryness of the mouth—is significantly more favorable than that of clonidine [2-(2,6-dichloroanilino)-2-imidazoline], a structurally closely related known compound with equal antihypertensive efficacy, as shown by the following comparison:

The hypotensive activity of the test compounds was determined on a statistically significant number of rabbits under urthane anesthesia. The blood pressure of the test animals was continuously measured in the arteria carotis by means of a mercury manometer before and after the i.v. administration of the test compound at varying dosage levels. The $ED_{20}$ was determined, that is, the dose which produced a lasting reduction of 20 mm Hg of the blood pressure.

The effect on the stomach juice secretion was determined on rats by the standard test method of Shay et al, Gastroenterology 5, 43 (1943), and the $ED_{50}$ was calculated for each test compound, that is, the dose which reduces the volume of stomach juice secreted over a given amount of time by 50%, and at the same time produces a 50% reduction in the total acidity of the secreted stomach juice volume. The following table shows the results which were obtained from these tests:

| Compound | Hypotensive $ED_{20}$ in rabbits, mgm/kg | Stomach juice secretion inhibiting $ED_{50}$ in rats, mgm/kg |
|---|---|---|
| Clonidine . HCl | 0.01 | 0.04 |
| 2-Bromo-6-fluoro-N-(2-imidazolidin-ylidene)-benzamine . HCl | 0.01 | 0.1 |

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective antihypertensive dosage unit of the compounds according to the present invention is from 0.00083 to 0.5 mgm/kg body weight, preferably 0.0016 to 0.167 mgm/kg body weight.

The following examples illustrated a few pharmaceutical dosage unit compositions comprising a compound of the present invention as an active ingredient and represent the best modes contemplated of putting the invention into practical use. The parts are parts by weight unless otherwise specified.

EXAMPLE 2

Tablets
The tablet composition is compounded from the following ingredients:

| | |
|---|---|
| 2-Bromo-6-fluoro-N-(2-imidazolidinylidene)-benzamine . HCl | 0.15 parts |
| Corn starch | 160.00 parts |
| Sec. calcium phosphate | 250.00 parts |
| Magnesium stearate | 9.85 parts |
| Total | 420.00 parts |

Preparation
The individual ingredients are intimately admixed with each other, the mixture is granulated, and the granulate is compressed into 420 mgm-tablets in a conventional tablet making machine. Each tablet contains 0.15 mgm of the active ingredient and is an antihypertensive oral dosage unit composition.

EXAMPLE 3

Gelatin capsules
The capsule filler composition is compounded from the following ingredients:

| | |
|---|---|
| 2-Bromo-6-fluoro-N-(2-imidazolidinylidene)-benzamine . HCl | 0.3 parts |
| Corn starch | 199.7 parts |
| Total | 200.0 parts |

Preparation
The ingredients are intimately admixed with each other, and 200 mgm-portions of the mixture are filled into gelatin capsules of suitable size. Each capsule contains 0.3 mgm of the active ingredient and is an antihypertensive oral dosage unit composition.

EXAMPLE 4

Hypodermic solution
The solution is compounded from the following ingredients:

| | |
|---|---|
| 2-Bromo-6-fluoro-N-(2-imidazolidinylidene)-benzamine . HCl | 1.5 parts |
| Sodium salt of EDTA | 0.2 parts |
| Distilled water q.s.ad | 100.0 parts |

Preparation
The active ingredient and the EDTA salt are dissolved in a sufficient amount of distilled water, and the solution is diluted with additional distilled water to the desired volume. The resulting solution is filtered until free from suspended particles, and the filtrate is filled into 2 cc-ampules under aseptic conditions. The filled ampules are finally sterilized and sealed. Each ampule contains 30 mgm of the active ingredient, and the contents thereof are an injectable antihypertensive dosage unit composition.

The free base or any other non-toxic acid addition sale of 2-bromo-6-fluoro-N-(2-imidazolidinylidene)-benzamine may be substituted for the hydrochloride in Examples 2 through 4. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. 2-Bromo-6-fluoro-N-(2-imidazolidinylidene)-benzamine or a non-toxic, pharmacologically acceptable acid addition salt thereof.
2. An antihypertensive pharmaceutical dosage unit composition consisting essentially of an inert pharmaceutical carrier and an effective antihypertensive amount of a compound of claim 1.
3. The method of lowering the blood pressure of a warm-blooded animal in need thereof, which comprises perorally or parenterally administering to said animal an effective antihypertensive amount of compound of claim 1.

* * * * *